US012578297B2

(12) United States Patent
Wang et al.

(10) Patent No.: US 12,578,297 B2
(45) Date of Patent: Mar. 17, 2026

(54) CIRCUIT OF ELECTROCHEMICAL SENSOR, AND METHOD AND DEVICE

(71) Applicant: ZHEJIANG E-LINKCARE MEDITECH CO., LTD., Zhejiang (CN)

(72) Inventors: Tianxing Wang, Zhejiang (CN); Xijiang Hu, Zhejiang (CN); Ziyi Zhang, Zhejiang (CN)

(73) Assignee: ZHEJIANG E-LINKCARE MEDITECH CO., LTD., Zhejiang (CN)

( * ) Notice: Subject to any disclaimer, the term of this patent is extended or adjusted under 35 U.S.C. 154(b) by 652 days.

(21) Appl. No.: 18/040,720

(22) PCT Filed: Jun. 23, 2021

(86) PCT No.: PCT/CN2021/101840
§ 371 (c)(1),
(2) Date: Feb. 6, 2023

(87) PCT Pub. No.: WO2021/259328
PCT Pub. Date: Dec. 30, 2021

(65) Prior Publication Data
US 2025/0297984 A1 Sep. 25, 2025

(30) Foreign Application Priority Data

Jun. 24, 2020 (CN) .......................... 202010593911.5

(51) Int. Cl.
*G01N 27/406* (2006.01)
*A61B 5/08* (2006.01)
(Continued)

(52) U.S. Cl.
CPC ......... *G01N 27/4065* (2013.01); *A61B 5/082* (2013.01); *A61B 5/097* (2013.01); *G01N 27/407* (2013.01)

(58) Field of Classification Search
CPC . A61B 5/082; A61B 5/097; A61B 2560/0209; A61B 5/1468; A61B 5/7225;
(Continued)

(56) References Cited

U.S. PATENT DOCUMENTS 8,926,809 B2 1/2015 Pletcher et al.
9,392,171 B2 7/2016 Uemura et al.
(Continued)

FOREIGN PATENT DOCUMENTS

CN 202599895 U 12/2012
CN 102981426 A 3/2013
(Continued)

OTHER PUBLICATIONS

International Search Report issued in PCT/CN2021/101840 on Sep. 24, 2021 (8 pages).

*Primary Examiner* — Jennifer Wecker
*Assistant Examiner* — Jonathan Bortoli
(74) *Attorney, Agent, or Firm* — Michael A. Whittaker

(57) ABSTRACT

The invention relates to a circuit for an electrochemical sensor and a usage method for the circuit. The circuit includes an electrochemical sensor, a control circuit and a measurement circuit, and a changeover switch is arranged between the control circuit and the measurement circuit. The control circuit provides a bias voltage for electrodes of the electrochemical sensor, is a low-power-consumption circuit, and includes a low-power-consumption operational amplifier. The measurement circuit includes a low-noise and high-precision operational amplifier, and is used to detect signals when the electrochemical sensor is in operation.

(Continued)

When the electrochemical sensor is not in operation, the stability of the sensor can be maintained, and the problems that batteries are replaced frequently due to excessively fast power consumption and a long stabilization time is required by the sensor after the batteries are replaced can also be avoided; and when the electrochemical sensor is in operation, low noise and high precision of a measurement result are guaranteed. The circuit has low power consumption and high detection precision, and can be applied to detection, performed by means of the electrochemical sensor, of a gas concentration such as a nitric oxide concentration in expiratory gas.

11 Claims, 7 Drawing Sheets

(51) Int. Cl.
*A61B 5/097* (2006.01)
*G01N 27/407* (2006.01)

(58) Field of Classification Search
CPC . G01N 27/4065; G01N 27/407; G01N 27/416
See application file for complete search history.

(56) References Cited

U.S. PATENT DOCUMENTS

| 2014/0209481 A1 | 7/2014 | Pletcher et al. |
| 2014/0213867 A1 | 7/2014 | Pletcher et al. |
| 2015/0077579 A1 | 3/2015 | Uemura et al. |
| 2018/0292550 A1* | 10/2018 | Xu ......................... G01R 31/14 |

FOREIGN PATENT DOCUMENTS

| CN | 104246432 A | 12/2014 |
| CN | 105102971 A | 11/2015 |
| CN | 205193002 U | 4/2016 |
| CN | 108645906 A | 10/2018 |
| CN | 212904653 U | 4/2021 |
| JP | 2013092437 A | 5/2013 |

* cited by examiner

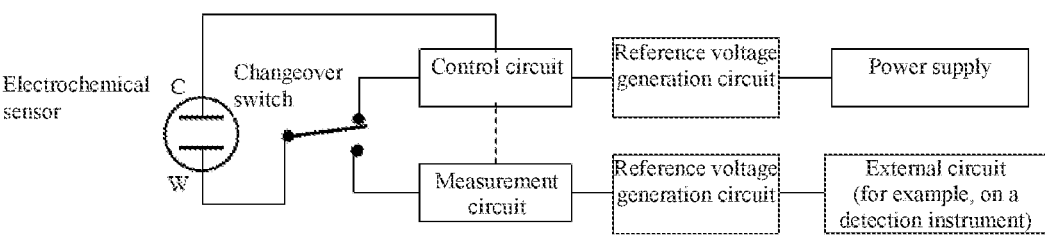

FIG. 5

(1) Before usage, a bias voltage is applied to an electrochemical sensor and maintained by a control circuit; and after a period of time, a baseline current of the electrochemical sensor is stable.

↓

(2) During a test or when a detection instrument has a large-capacity power supply/external power supply, a measurement circuit is used to detect signals of the electrochemical sensor.

↓

(3) After the test ends or the detection instrument is powered off, the control circuit is used to maintain the bias voltage for the electrochemical sensor in a low-power-consumption manner.

FIG. 6

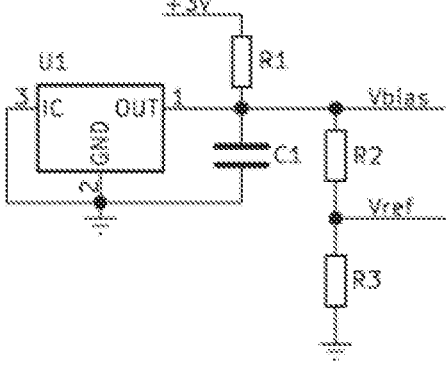

FIG. 7

CIRCUIT OF ELECTROCHEMICAL SENSOR, AND METHOD AND DEVICE

CROSS-REFERENCE TO RELATED APPLICATIONS

The present invention is filed under 35 U.S.C. § 371 as the U.S. national phase of International Application No. PCT/CN2021/101840, filed Jun. 23, 2021, which designated the United States and claims the benefit of priority of Chinese Patent Application No. 202010593911.5 filed Jun. 24, 2020, the contents of each of which are being hereby incorporated by reference in their entirety for all purposes.

FIELD OF TECHNOLOGY

The present invention relates to the field of circuit design, in particular to a design and usage method for a circuit for an electrochemical sensor, and detection equipment based on the circuit.

BACKGROUND OF THE INVENTION

Electrochemical sensors have multiple advantages such as high efficiency, convenience, sensitivity, speediness, easy miniaturization, integration, low power consumption and the like. In recent years, with the rapid development of related disciplines and technologies such as electrochemistry, material science, biology and the like, the electrochemical sensors have been widely applied in fields of automobile industry, environment monitoring, food safety, clinical diagnosis and the like.

The working principle of the electrochemical sensor is to place a substance to be tested in a proper form in an electrochemical reaction zone and measure changes of electrochemical parameters (such as potential, current and conductivity) so as to determine the content of the substance to be tested. The electrochemical sensors may be divided into potential type sensors, current type sensors and conductivity type sensors according to their different output signals.

The current type electrochemical sensors are very widely used, and some gas sensors, such as carbon monoxide sensors, nitric oxide sensors and oxygen sensors, and biological sensors, such as blood glucose test strips, blood ketone test strips and uric acid test strips, are all based on the principle of the current type sensors. The simplest form of such sensors is a two-electrode system composed of a working electrode (sensitive electrode) and a counter electrode, and the two electrodes are separated by a thin-layer electrolyte. After a sample to be tested enters the sensor, an oxidation or reduction reaction is carried out on the surface of the working electrode to generate a current which flows through the two electrodes through an external circuit. The generated current is in direct proportion to the concentration of the sample to be tested, and the external circuit calculates the concentration of the sample to be tested by measuring the current.

In order to achieve the reaction, potential of the working electrode is required to be kept within a specific range, so a relative bias voltage is required to be maintained between the working electrode and the counter electrode (or a reference electrode) for certain electrochemical sensors. After a new bias voltage is applied, some electrochemical sensors, for example, the nitric oxide sensors will generate a relatively large and quickly decreasing baseline signal and need a relatively long time for stabilization, which is generally 24 hours or longer. Therefore, for such electrochemical sensors, manufacturers usually configure bias voltage control circuits on the sensors when the products are delivered, and the circuits are powered by batteries so as to ensure that the sensors are "ready for work". In addition, in the prior art, signal measurement circuits are also powered by the batteries for long-term working together with the bias voltage control circuits, so it is not necessary to spend time waiting for stabilization of the sensors when the sensors operate for measurement.

Generally, there is no problem in the prior art. However, some tests performed by means of such electrochemical sensors are required to be applied to scenes of testing trace amounts of samples to be tested, for example, testing the nitric oxide concentration in expiratory gas, since the concentrations of the samples to be tested are very low, measurement signals are very weak, but relatively high measurement precision is required in the clinical application, which requires that the measurement circuits have good performance, including relatively low measurement noise, relatively high signal-to-noise ratios and high measurement precision. Therefore, according to the requirements of the measurement performance, it is generally required to select high-performance components (including operational amplifiers) with low noise and high precision; however, such components generally have relatively high power consumption, if the prior art is used, the high-performance operational amplifiers are also powered by the batteries for long-term working together with the bias voltage control circuits, and the energy of the batteries will be consumed quickly. Therefore, when the products are delivered to users, the batteries of the control circuits are often exhausted, and the users have to replace the batteries and spend a long time enabling the sensors to be stabilized again to be "ready for work"; and this situation also appears in the actual usage process after the users mount the sensors, and after the batteries of the control circuits are exhausted, the users have to disassemble the instruments to replace the batteries of the sensors and spend a long time waiting for stabilization of the sensors, or require engineers of the manufacturers to perform maintenance. Thus, the products are very inconvenient to use, the usage cost is greatly increased, the usage efficiency of the products is very low, and some manufacturers even directly limit the service life of the products.

Currently, in order to solve this problem, some solutions have also been tried in the industry, for example, the high-precision components such as low-noise and high-precision operational amplifiers are used in the control circuits. However, those skilled in the art all know that when the precision of the operational amplifiers is improved a little, the power consumption will be directly multiplied. Therefore, large-capacity batteries must be used. However, this solution not only increases the cost, but also makes it difficult to miniaturize the design of the sensors. There are also some solutions that make compromises, that is, components (including operational amplifiers) with medium performance are used in the measurement circuits, which can indeed reduce the consumption speed of the batteries and prolong the service life of the batteries; however, the performance of measurement signals is also remarkably sacrificed, and even the performance of the products cannot meet usage requirements.

Therefore, according to technical characteristics of such electrochemical sensors and technical requirements of practical applications, there is an urgent need for a new technical solution, which can maintain the low-power-consumption bias voltage when the sensors are not in operation so as to ensure that the sensors are "ready for work" while prolonging the duration of the state, and can also provide the good measurement performance when the sensors are in operation. This will be of great significance.

SUMMARY OF THE INVENTION

In order to solve the problems and defects in the prior art, the present invention provides a circuit solution for an electrochemical sensor and a usage method, which aim to maintain a bias voltage of the electrochemical sensor by means of a low-power-consumption control circuit so as to enable the sensor to be "ready for work" when the electrochemical sensor is not in operation, and the low-power-consumption control circuit can effectively reduce the consumption speed of battery power, prolong the duration of the state that the sensor is "ready for work", improve the convenience in usage of the product and reduce the usage cost of the product; and on the other hand, when the sensor is in operation, a high-performance measurement circuit is used to ensure the precision of electric test signals.

In order to achieve the purposes of the present invention, the present invention provides a circuit for an electrochemical sensor, the circuit comprising a control circuit and a measurement circuit, wherein the control circuit is used to maintain a bias voltage of the electrochemical sensor, and the measurement circuit is used to detect signals when the electrochemical sensor is in operation; an operational amplifier U2 is arranged on the control circuit and connected to a working electrode of the sensor; an operational amplifier U3 is arranged on the measurement circuit and electrically connected to the working electrode of the sensor; the operational amplifier U2 has power consumption lower than that of the operational amplifier U3; the operational amplifier U3 produces noise lower than that produced by the operational amplifier U2; and a changeover switch is arranged between the control circuit and the measurement circuit.

Further, the operational amplifier U3 has precision higher than that of the operational amplifier U2.

The present invention further provides a circuit for an electrochemical sensor, the circuit comprising a control circuit and a measurement circuit, wherein the control circuit is used to maintain a bias voltage of the electrochemical sensor, and the measurement circuit is used to detect signals when the electrochemical sensor is in operation; an operational amplifier U2 is arranged on the control circuit and connected to a working electrode of the sensor; an operational amplifier U3 is arranged on the measurement circuit and electrically connected to the working electrode of the sensor; the operational amplifier U3 has precision higher than that of the operational amplifier U2; the operational amplifier U3 produces noise lower than that produced by the operational amplifier U2; and a changeover switch is arranged between the control circuit and the measurement circuit.

Further, the operational amplifier U2 has power consumption lower than that of the operational amplifier U3.

The present invention further provides a circuit for an electrochemical sensor, the circuit comprising a control circuit and a measurement circuit, wherein the control circuit is used to maintain a bias voltage of the electrochemical sensor, and the measurement circuit is used to detect signals of the sensor during sample analysis; the control circuit has power consumption lower than that of the measurement circuit; and a changeover switch is arranged between the control circuit and the measurement circuit. When the electrochemical sensor is not in operation, the control circuit is used to maintain the bias voltage of the sensor; and when the electrochemical sensor is in operation, the measurement circuit is used.

Specifically, the circuit for the electrochemical sensor comprises the control circuit and the measurement circuit, and the changeover switch is arranged between the control circuit and the measurement circuit. The control circuit is a low-power-consumption circuit, provides the bias voltage between a working electrode (and an auxiliary electrode) and a reference electrode (or a counter electrode) of the electrochemical sensor, and at least includes one low-power-consumption operational amplifier; and the measurement circuit is used to detect the signals when the electrochemical sensor is in operation and at least includes a low-noise and high-precision operational amplifier. FIG. 5 shows an example of the connection manner of various units of the present invention. A power supply is connected to the electrochemical sensor by means of a reference voltage generation circuit, the control circuit and the changeover switch so as to maintain the bias voltage between the working electrode W and the counter electrode C for the electrochemical sensor; a reference voltage generation circuit and the measurement circuit are connected to the electrochemical sensor by means of the changeover switch; dotted lines in the figure represent that the measurement circuit may not share or share a part of the circuit with the control circuit; and the reference voltage generation circuit and the other end of the measurement circuit are connected to an external circuit, the external circuit may be arranged on a detection instrument, and the measurement circuit may use a power supply of the external circuit and detect reaction signals of the electrochemical sensor together with the external circuit. The reference voltage generation circuit is a well-known technology in the art, and an example of the circuit is as shown in FIG. 7.

The present invention further provides a method for reducing power consumption of a circuit for an electrochemical sensor, the circuit comprising a control circuit and a measurement circuit, wherein the control circuit is used to maintain a bias voltage of the sensor, and the measurement circuit is used to detect signals of the sensor during sample analysis; the control circuit has power consumption lower than that of the measurement circuit, when the electrochemical sensor is not in operation, the control circuit is used to maintain the bias voltage of the sensor; and when the electrochemical sensor is in operation, the measurement circuit is used.

Specifically, the usage method based on the circuit is as follows: when the electrochemical sensor is not in operation, only the low-power-consumption control circuit is used to maintain the bias voltage of the sensor so as to enable the sensor to be "ready for work"; and when the electrochemical sensor is in operation, the measurement circuit is used so as to ensure the precision of measurement signals. When the measurement circuit is used, the control circuit may not be in operation and may be in operation partially, preferably be in operation partially. In some embodiments, when there is a large-capacity battery or an external power supply, for example, when the sensor is mounted on a detection instrument and the instrument is started for operation, the measurement circuit can be used, and the large-capacity battery of the detection instrument can be used; and after the instrument is powered off, the control circuit is used to maintain the bias voltage of the electrochemical sensor in a low power consumption state. Thus, repeated switching during detection and after detection in the actual usage process can be avoided.

According to different application scenes of the solutions of the present invention, the embodiments may be transformed as follows: (1) the electrochemical sensor is not configured with the circuit during storage and transportation, and the circuit is arranged in the detection instrument applying the electrochemical sensor; (2) the electrochemical sensor is configured with the control circuit during storage and transportation and comprises the changeover switch, and the detection instrument applying the electrochemical sensor is configured with the measurement circuit; and (3) the electrochemical sensor is configured with the circuit during storage and transportation, the circuit comprises the control circuit, the measurement circuit and the changeover switch, and the detection instrument applying the electrochemical sensor can directly use the circuit for the electrochemical sensor.

The control circuit needs to provide the bias voltage for the electrochemical sensor. The double-electrode electrochemical sensor is used as an example (as shown in FIG. 1a), double electrodes are the working electrode (sensitive electrode) and the counter electrode (also having the effects of the reference electrode in the double-electrode sensor) respectively. The control circuit needs to provide a reference voltage Vref for the counter electrode C of the sensor by means of an operational amplifier U1 firstly (as shown in 100a of FIG. 1a) and then provides another voltage Vbis for the working electrode W of the sensor by means of another operational amplifier U2 (as shown in 200a of FIG. 1a), and there is a deviation between the voltage and the reference voltage, that is, the bias voltage. In some embodiments, in the double-electrode sensor, the reference voltage Vref can be provided for the counter electrode C without the operational amplifier U1, and the reference voltage Vref can be directly provided for the counter electrode by means of the reference voltage generation circuit of the external circuit.

As shown in FIG. 1a, the sensor comprises the working electrode and the counter electrode, the working electrode is connected to a circuit 200a, the counter electrode is connected to a circuit 100a, and when U2 on the circuit 200a is a high-performance component, a formed loop is the prior art mentioned in the background, is used as the measurement circuit (100a and 200b) for the sample to be tested, and is also used as the control circuit (100a and 200b) for maintaining the bias voltage of the sensor. In the prior art, the reaction signals need to be detected at the working electrode W end when the sensor is in operation, so the circuit 200a may have the functions of the measurement circuit, that is, the operational amplifier U2 includes an I/V conversion amplifying circuit (R2, R3, C1), and a signal Vwork1 is output at an output end 7 of the operational amplifier U2. Such situation, the operational amplifier U2 must be the high-performance component with low noise and high precision, and such operational amplifier generally has relatively high power consumption, so that the power of the battery of the sensor may be consumed quickly when the bias voltage is maintained for the sensor by such circuits (100a and 200a in FIG. 1a, and 200a including a test function).

Therefore, an independent measurement circuit 210 is introduced into the present invention on the basis of the circuits 100a and 200a in the prior art and is switched by means of the changeover switch 900. In one embodiment, the design of the measurement circuit 210 may be similar to that of the circuit 200a; however, the operational amplifier U2 of the circuit 200a is the low-power-consumption component, and the operational amplifier U3 of the measurement circuit 210 needs to be the above-mentioned high-performance component with low noise and high precision, which has the relatively high power consumption. The measurement circuit in the present invention also needs a reference potential circuit of the counter electrode, and a loop is formed. In one embodiment, the measurement circuit can be independent of the circuit 100a to be separately provided with the reference potential of the counter electrode and the loop. However, if the performance requirements can also be met when an original reference potential circuit of the counter electrode in the prior art is directly used and the loop is formed, the circuit 100a on the original counter electrode can be used, and under the condition that the performance meets the requirements, the solution is preferred so as to reduce the cost. As described above, the circuit 200a of the present invention can be combined with the circuit 100a to just maintain the bias voltage when the electrochemical sensor is not in operation, that is, the control circuit and the operational amplifiers U1 and U2 can be low-power-consumption components; and when the sensor is in operation, the circuit is switched from the circuit 200a to the circuit 210 by means of the changeover switch 900, and the circuit 210 and the circuit 100a constitute the measurement circuit of the present invention. Since the additional measurement circuit 210 is introduced, the measurement function of the circuit 200a is not required, as shown in 200b of FIG. 1b (no including the IN conversion amplifying circuit and free from components such as R3 and C1), as a preferred embodiment of the present invention, the control circuit may not include the IN conversion amplifying circuit having the measurement function.

When the double-electrode electrochemical sensor is in operation, the sample to be tested is subjected to a reaction on the working electrode and generates a current, resulting in change of the potential of the counter electrode (a polarization phenomenon), and resulting in change of the bias voltage between the working electrode and the counter electrode; when the concentration of the sample to be tested is increased, the reaction current is also increased; and with the continuous increase of the concentration of the sample to be tested, the potential of the working electrode will exceed the permissible range finally, resulting in the non-linear response of the sensor. Therefore, in order to solve the problem, the third electrode (reference electrode R) is introduced into some electrochemical sensors, which are so-called three-electrode electrochemical sensors. In one of the three-electrode electrochemical sensors, a reference voltage is applied to the reference electrode, and no current flows through the reference electrode when the sensor is in operation, so the potential of the reference electrode is constant; a bias voltage is applied to the working electrode, and the sample to be tested is subjected to a reaction on the working electrode and generates a current; and the counter electrode is mainly used to form a loop and perform a corresponding reaction on the electrode. Since the potential of the reference electrode is constant, the bias voltage between the working electrode and the reference electrode is also constant, which effectively eliminates the influence of the polarization phenomenon. For the three-electrode electrochemical sensors, the circuit design of the present invention is similar to that of the double-electrode electrochemical sensor, except that the reference potential is applied to the reference electrode and a constant-potential circuit is introduced, as shown in FIG. 2a and FIG. 2b. Since the independent measurement circuit is introduced into the present invention, FIG. 2b is used as an optimized solution of FIG. 2a, a measurement module (including the I/V conversion amplifying circuit and components such as R4 and C2) of the circuit 200a in FIG.

2*a* is removed, and the circuit 200*b* in FIG. 2*b* is formed. According to the technical solutions of the present invention, in FIG. 2*a* and FIG. 2*b*, the operational amplifiers U1, U2 may be the low-power-consumption components, the operational amplifier U3 needs to be the high-performance component with low noise and high precision. The circuit 200*a* (or 200*b*) and the circuit 100*b* constitute the control circuit, and the circuit 210 and the circuit 100*b* constitute the measurement circuit; and the control circuit and the measurement circuit are switched by means of the changeover switch (900).

In order to eliminate the influence of the temperature on a baseline current of the working electrode, the fourth electrode (auxiliary electrode A) is introduced into some electrochemical sensors introduce, which are so-called four-electrode electrochemical sensors. The design of the auxiliary electrode is the same as that of the working electrode, but the auxiliary electrode is not exposed to the sample to be tested; therefore, the influence of the temperature on the baseline current of the working electrode can be eliminated by subtracting a signal of the auxiliary electrode from a signal of the working electrode. According to the technical solutions of the present invention, for the auxiliary electrode, the bias voltage relative to the reference electrode is applied to the control circuit, and a module for measuring the signal of the auxiliary electrode is needed in the measurement circuit, as shown in FIG. 3*a* and FIG. 3*b*. FIG. 3*b* is an optimized solution of FIG. 3*a*, and the unnecessary measurement module is removed from the control circuit. According to the technical solutions of the present invention, the operational amplifiers U1, U2, U4 in FIG. 3*a* and FIG. 3*b* may be the low-power-consumption components, the operational amplifiers U3, U5 in FIG. 3*a* and FIG. 3*b* need to be the high-performance components with low noise and high precision. The circuits 100*b*, 200*a* (or 200*b*), 300*a* (or 200*b*) constitute the control circuit, and the circuits 100*b*, 210, 310 constitute the measurement circuit; and the control circuit and the measurement circuit are switched by means of the changeover switches 900*a*. 900*b*.

In one embodiment, the control circuit and the measurement circuit may also share a circuit connected to the operational amplifier U1.

The changeover switch may be realized in many manners and is often a relay, a field effect transistor, an analog switch or a triode.

Usually, the electrochemical sensor is used as a replaceable component and consumable of the detection instrument and is a separate unit in the processes of product output, delivery, storage and transportation; besides, the user usually hopes to receive the sensor that is "ready for work", so as to improve the convenience in usage. Therefore, the control circuit needs to comprise at least one power supply to supply power to the control circuit so as to maintain the bias voltage of the sensor. The power supply is the battery, including but not limited to a button battery, an alkaline battery and a rechargeable battery. Preferably, the button battery is a relatively good choice, which can minimize the occupied volume of the battery, facilitate the miniaturization of the design of the product and reduce the packaging and transportation costs of the product.

Of course, some users can accept that the electrochemical sensor needs a relatively long stabilization time when it is used for the first time, but hope that the electrochemical sensor can maintain a relatively long service life after it is mounted for the first time, so the power supply of the control circuit may be implemented in following manners: (1) no battery is preset, and the battery is mounted immediately when the user uses the sensor; and (2) a built-in power supply (that is, the external power supply of the circuit) on the detection instrument is directly used. With regard to the second manner, after the sensor is mounted, the control circuit is directly connected with the built-in power supply of the detection instrument for power supply, and the bias voltage is provided for the sensor. Usually, the built-in power supply of the detection instrument may be the large-capacity battery (including the rechargeable battery), through combination with the circuit solution of the present invention, the state that the sensor is "ready for work" may be continued to the maximum extent, and the purposes that the battery is not required to be replaced for maintenance after mounting and the sensor can work in real time are achieved. However, built-in power supplies of some detection instruments usually need to supply power to a plurality of functions, and the possibility of accidental exhausting cannot be excluded, so the first manner is suitable in this situation.

According to the actual application requirements of the products, some products adopt the portable design of integrating electrochemical sensors and detection instruments. With regard to such design, the circuit of the electrochemical sensor may be designed to be integrated with the detection instrument and may also be designed separately. In addition, such detection instrument is usually configured with the built-in power supply having the relatively high power, for example, the rechargeable battery, so the power supply of the control circuit may directly be the built-in power supply of the detection instrument, that is, the external power supply of the circuit. Similarly, the built-in power supply of the detection instrument usually supplies power to multiple functions, so the separate built-in power supply can also be arranged in the control circuit so as to prevent accidental power outage of the control circuit of the sensor due to exhausting of the built-in power supply of the detection instrument due to excessive usage by other functions.

On the basis of the circuit design mentioned above, a usage method for the electrochemical sensor is as follows: when the electrochemical sensor is not in operation, only the low-power-consumption control circuit is used to maintain the bias voltage of the sensor so as to slow down the consumption of the power of the battery, prolong the duration that the sensor is "ready for work" and improve the usage efficiency and usage convenience of the sensor; and when the electrochemical sensor is in operation, the measurement circuit is used by means of the changeover switch so as to ensure the precision of test results. When part of the control circuit can meet the measurement requirement, the measurement circuit can use part of the control circuit, so when the measurement circuit is used, the control circuit can be in operation partially.

The present invention further provides detection equipment comprising an electrochemical sensor, the equipment comprising the electrochemical sensor of the present invention and a detection instrument.

In some embodiments, a control circuit, a measurement circuit, a changeover switch and the electrochemical sensor are set as equipment components; and during usage, the equipment components and the detection instrument are assembled together.

The present invention relates to a circuit for an electrochemical sensor and a usage method for the circuit. The circuit comprises the electrochemical sensor, a control circuit and a measurement circuit, and a changeover switch is arranged between the control circuit and the measurement circuit. The control circuit provides a bias voltage for electrodes of the electrochemical sensor, is a low-power-consumption circuit, and includes a low-power-consumption operational amplifier. The measurement circuit includes a low-noise and high-precision operational amplifier, and is used to detect signals when the electrochemical sensor is in operation.

The present invention further provides detection equipment for analyzing a specific component in expiratory gas, the equipment comprising a breathing handle, a detection equipment host and a specific component detector, wherein the specific component detector comprises an electrochemical sensor for detecting a specific component and a circuit connected to the electrochemical sensor in the present invention.

Further, the detection equipment host comprises a detector mounting recess, and the specific component detector is mounted in the detector mounting recess. Further, the breathing handle is connected to a gas passage of the detection equipment host by means of a gas guiding tube.

The specific component in the gas is selected from nitric oxide, carbon monoxide, hydrogen, ammonia gas, hydrogen sulfide or oxygen.

Further, the electrochemical sensor is used to measure nitric oxide and comprises a reference electrode, a counter electrode and a working electrode.

The present invention may generate good effects. The control circuit and the measurement circuit of the present invention have the different power consumption, and the control circuit has the power consumption lower than that of the measurement circuit. Experiments show that, no matter which one of the double-electrode electrochemical sensor, the three-electrode electrochemical sensor and the four-electrode electrochemical sensor is used, when the circuit of the present invention is used, the low power consumption can be achieved, meanwhile, the precision of the measurement signals is guaranteed, and a measurement curve is stable and free of significant fluctuations. For example, the operational amplifier of the control circuit is the low-power-consumption component, and the operational amplifier of the measurement circuit is the high-performance component with relatively high power consumption, low noise, high signal-to-noise ratio and high precision. When the electrochemical sensor is not in operation, only the low-power-consumption bias voltage control circuit is maintained, so the stability of the sensor can be maintained, and the problems that the power supply is replaced frequently due to excessively fast power consumption and a long stabilization time is required by the sensor after the power supply is replaced can also be avoided. When the electrochemical sensor is in operation, the measurement circuit is used to ensure the performance of the measurement result.

BRIEF DESCRIPTION OF THE DRAWINGS

FIG. 5: an example diagram of a connection relationship of various units of a technique of the present invention.

FIG. 6: an example diagram of a test flow of the technique of the present invention.

FIG. 7: an example diagram of a reference voltage generation circuit.

DESCRIPTION OF THE EMBODIMENTS

The technical solutions of the present invention are further described in detail below by means of embodiments in conjunction with accompanying drawings.

Embodiment 1

Figure 1A:
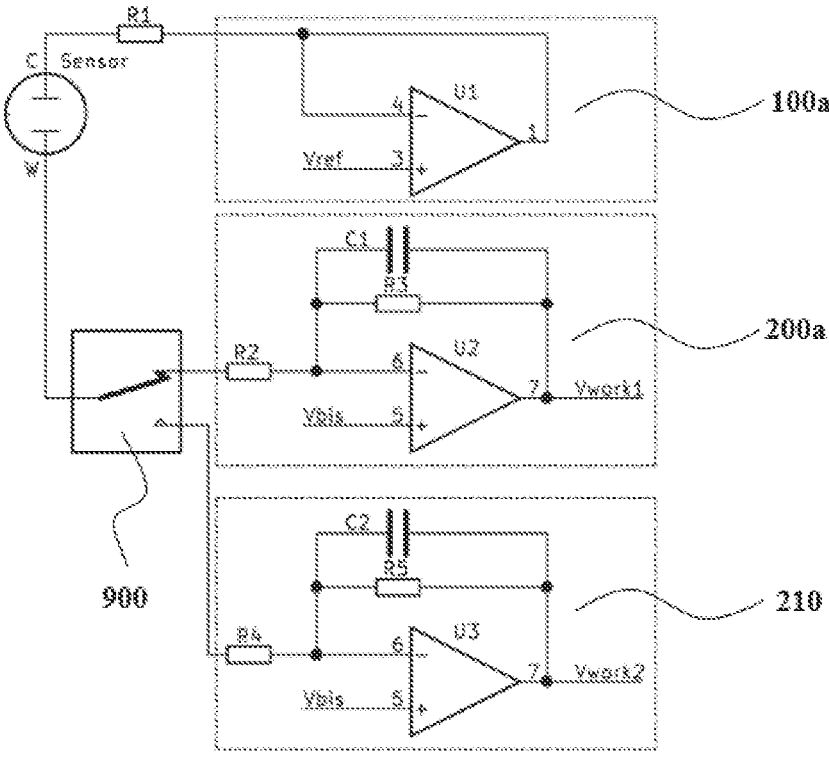
FIG. 1a: a schematic diagram of a circuit example of a double-electrode electrochemical sensor.
Figure 1B:
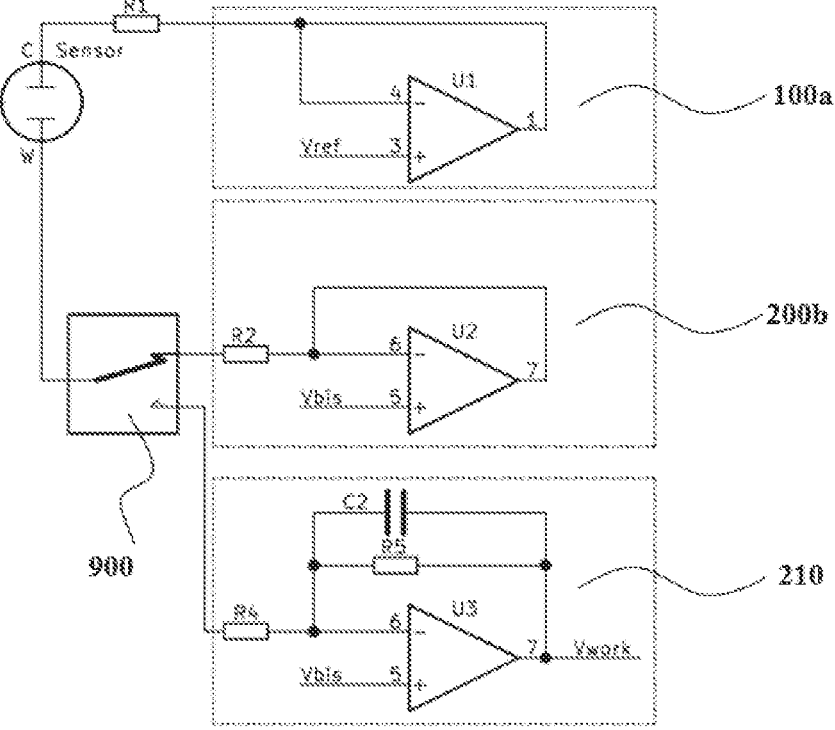
FIG. 1b: a schematic diagram of another circuit example of the double-electrode electrochemical sensor.

Embodiment 1 depicts a circuit for a double-electrode electrochemical sensor of the present invention and a usage method, and the circuit is as shown in FIG. 1b. Sensor refers to an electrochemical sensor, C refers to a counter electrode, and W refers to a working electrode. A reference voltage Vref is input to a non-inverting input end 3 of an operational amplifier U1 of a circuit 100a and is connected to the counter electrode C through an inverted input end 4 and an output end 1 of the operational amplifier U1. Another voltage V bis is input to a non-inverting input end 5 of an operational amplifier U2 of a circuit 200b and is connected to the working electrode W through an inverted input end 6 and an output end 7 of the operational amplifier U2 and a changeover switch 900. Vref is different from Vbis, so that a bias voltage is applied between the working electrode W and the counter electrode C. A bias voltage Vbis is input to a non-inverting input end 5 of an operational amplifier U3 of a circuit 210 and is connected to the working electrode W through an inverted input end 6 of the operational amplifier U3 and the changeover switch 900; and the operational amplifier U3 is connected to an I/V conversion amplifying circuit, for example, R4, R5 and C2 in the circuit 210, and output through an output end 7 of U3. The operational amplifiers U1, U2 may be low-power-consumption components, for example, operational amplifiers having working currents below 1 uA, and such operational amplifiers generally will produce low-frequency noise being higher than 3 uVpp at 0.1-10 Hz. The operational amplifier U3 needs to be a high-performance component with low noise, high signal-to-noise ratio and high precision, for example, an operational amplifier which produces low-frequency noise being lower than 1 uVpp at 0.1-10 Hz, and such component generally has a working current above 50 uA; and even an operational amplifier which produces low-frequency noise being lower than 0.5 uVpp at 0.1-10 Hz may further be selected, and such component generally has a working current above 100 uA, and power consumption is higher. When the sensor is not in operation, the working electrode is connected to the circuit 200b through the changeover switch 900, and maintains the bias voltage for the sensor by means of the control circuit (100a and 200b). When the sensor is in operation, the working electrode is connected to the circuit 210 through the changeover switch 900, and a reaction signal Vwork of the working electrode W is detected by means of the measurement circuit (100*a* and 210).

Embodiment 2

Figure 2A:
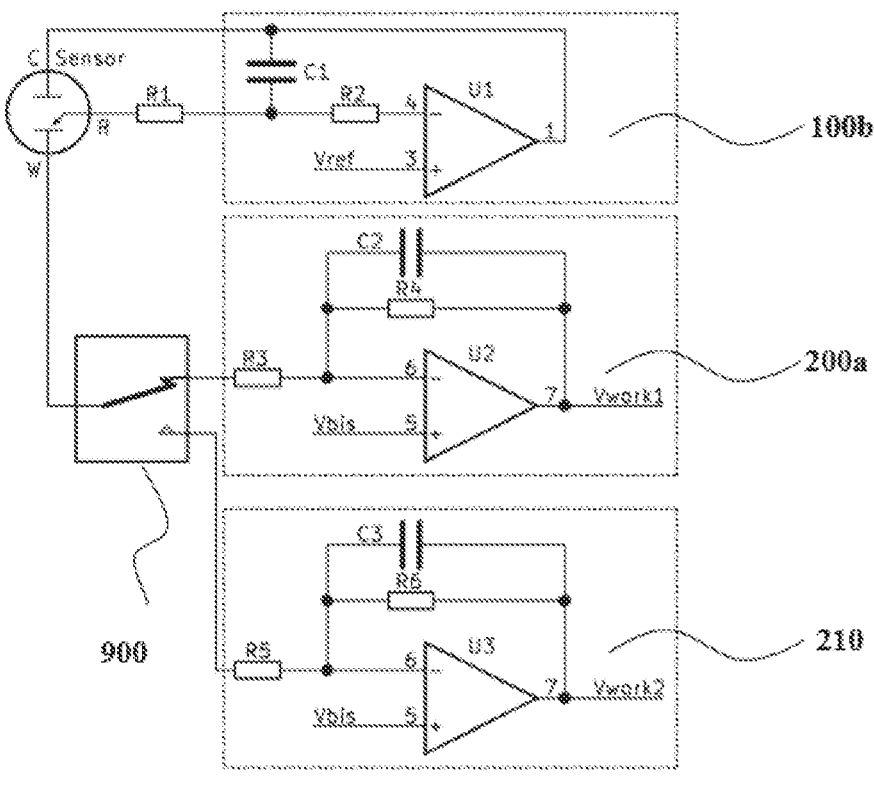
FIG. 2a: a schematic diagram of a circuit example of a three-electrode electrochemical sensor.
Figure 2B:
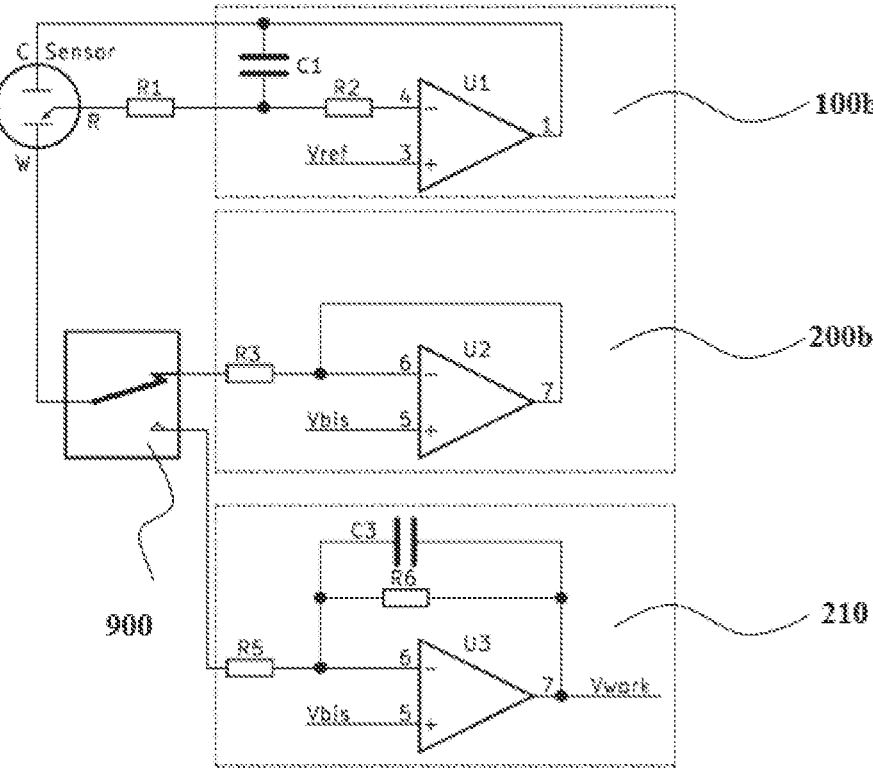
FIG. 2b: a schematic diagram of another circuit example of the three-electrode electrochemical sensor.

Embodiment 2 depicts a circuit for a three-electrode electrochemical sensor of the present invention and a usage method, and the circuit is as shown in FIG. 2*b*. Sensor refers to an electrochemical sensor, R refers to a reference electrode, C refers to a counter electrode, and W refers to a working electrode. A reference voltage Vref is input to a non-inverting input end 3 of an operational amplifier U1 of a circuit 100*b*, is connected to the reference electrode R through an inverted input end 4 of the operational amplifier U1, and is connected to the counter electrode C through an output end 7 of U1, so as to form a loop when the sensor is in operation. Another voltage Vbis is input to a non-inverting input end 5 of an operational amplifier U2 of a circuit 200*b* and is connected to the working electrode W through an inverted input end 6 and an output end 7 of the operational amplifier U2 and a changeover switch 900. A bias voltage Vbis is input to a non-inverting input end 5 of an operational amplifier U3 of a circuit 210 and is connected to the working electrode W through an inverted input end 6 of the operational amplifier U3 and the changeover switch 900; and the operational amplifier U3 is connected to an I/V conversion amplifying circuit, for example, R5, R6 and C3 in the circuit 210, and output through an output end 7 of U3. The operational amplifiers U1. U2 may be the low-power-consumption components as described in Embodiment 1; and the operational amplifier U3 needs to be the high-performance component as described in Embodiment 1. When the sensor is not in operation, the working electrode is connected to the circuit 200*b* through the changeover switch 900, and maintains the bias voltage for the sensor by means of the control circuit (100*b* and 200*b*); and when the sensor is in operation, the working electrode is connected to the circuit 210 through the changeover switch 900, and a reaction signal of the working electrode W is detected by means of the measurement circuit (100*b* and 210).

Embodiment 3

Figure 3A:
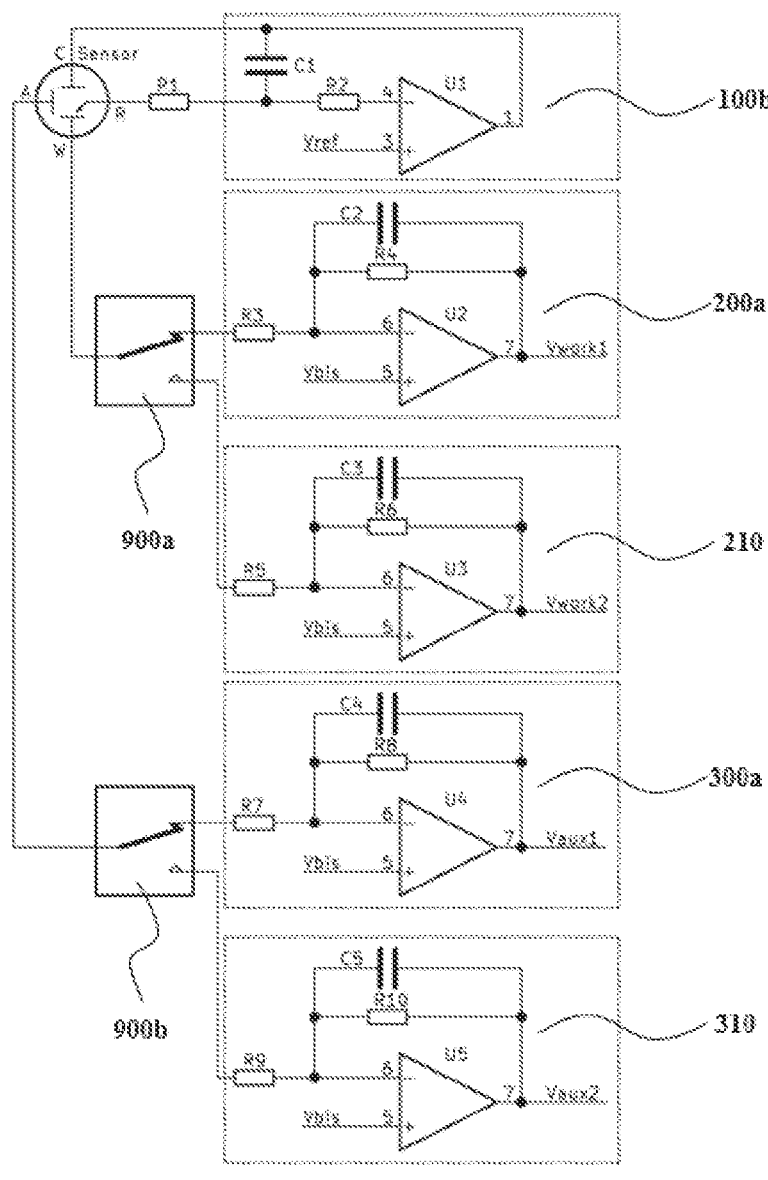
FIG. 3a: a schematic diagram of a circuit example of a four-electrode electrochemical sensor.
Figure 3B:
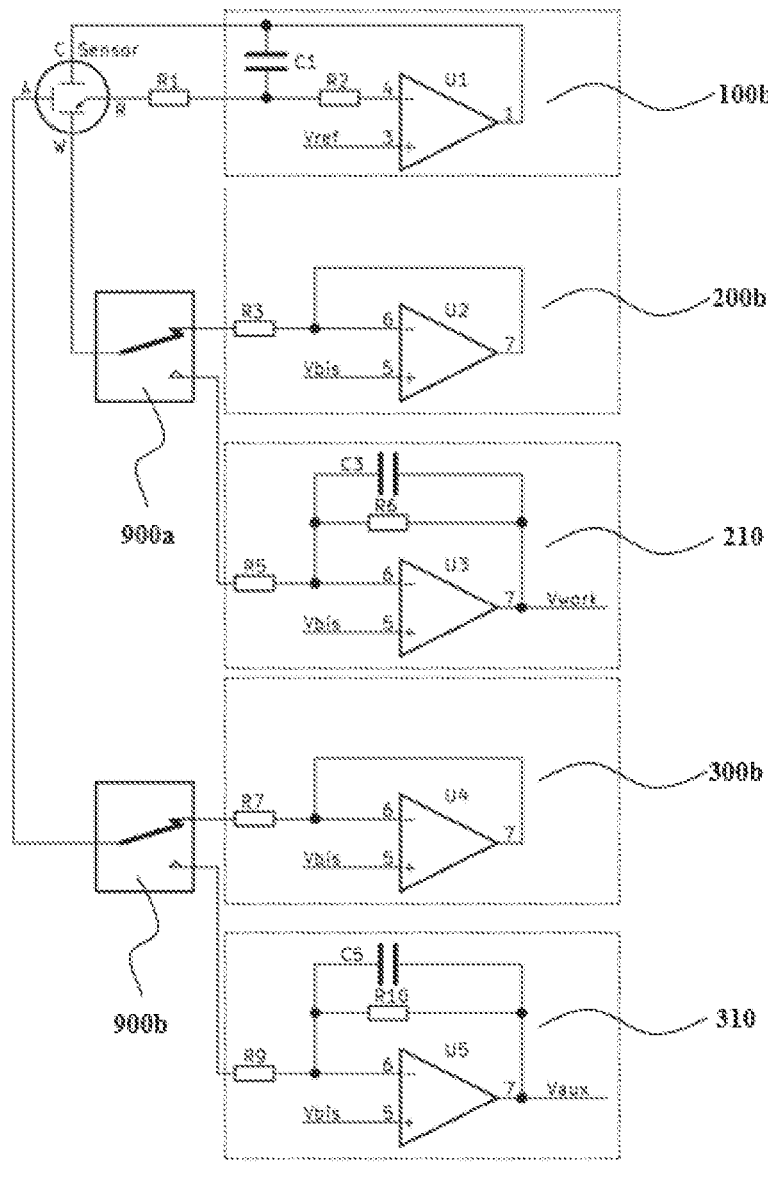
FIG. 3b: a schematic diagram of another circuit example of the four-electrode electrochemical sensor.

Embodiment 3 depicts a circuit for a four-electrode electrochemical sensor and a usage method, and the circuit is as shown in FIG. 3*b*. Sensor refers to an electrochemical sensor, R refers to a reference electrode, C refers to a counter electrode, W refers to a working electrode, and A refers to an auxiliary electrode. Embodiment 3 is basically the same as Embodiment 2, and the differences lie in that following circuits and a changeover switch need to be added to the auxiliary electrode A: a circuit 300*b* used to the auxiliary electrode A to maintain a bias voltage; a circuit 310 used for signal measurement of the auxiliary electrode A when the sensor is in operation; and a changeover switch 900*b* used for circuit switching of the auxiliary electrode when the sensor is in a standby mode and is in operation. Therefore, operational amplifiers U1, U2, U4 of this embodiment may be the low-power-consumption components as described in Embodiment 1; and the operational amplifiers U3, U5 need to be the high-performance components as described in Embodiment 1. Similarly, when the sensor is not in operation, the working electrode is connected to a circuit 200*b* through a changeover switch 900*a*, the auxiliary electrode is connected to the circuit 300*b* through the changeover switch 900*b*, and a bias voltage is maintained for the sensor by means of control circuits (100*b* and 200*b*, 100*b* and 300*b*); and when the sensor is in operation, the working electrode is connected to a circuit 210 and the circuit 310 respectively through the changeover switches 900*a* and 900*b*, and reaction signals of the working electrode W and the auxiliary electrode A are detected by means of measurement circuits (100*b* and 210, 100*b* and 310).

Embodiment 4: Comparison Embodiment

The comparison embodiment is achieved on a four-electrode electrochemical sensor, that is, the four-electrode electrochemical sensor, circuits 100*b*, 200*a*. 210, 300*a* and 310, and changeover switches 900*a* and 900*b* as shown in FIG. 3*a*. Operational amplifiers U1, U2, U4 are low-power-consumption components; and operational amplifiers U3. U5 are high-performance components.

Comparing FIG. 3*a* with FIG. 3*b*, the difference is the control circuits between the working electrode W and the auxiliary electrode A, for example, the measurement function is added to the circuits 200*a*. 300*a*.

Comparison solution 1: when the changeover switches (900*a*, 900*b*) in FIG. 3*a* are kept in states as shown in the figure, the circuits 100*b*, 200*a*, 300*a* are used as measurement circuits for detecting an sample to be tested, and are also used as control circuits for maintaining a bias voltage of the sensor. This solution is a low-power-consumption circuit solution in the prior art, and power consumption of the circuits and conditions of test precision are evaluated.

Comparison solution 2: when the changeover switches 900*a*. 900*b* in FIG. 3*a* are switched to the other side at the same time, the changeover switches 900*a*, 900*b* are respectively connected to the circuits 210 and 310 at this moment, that is, the circuits 100*b*. 210, 310 are used as measurement circuits for detecting an sample to be tested, and are also used as control circuits for maintaining the bias voltage of the sensor. This solution is a low-noise circuit solution in the prior art, and power consumption of the circuits and conditions of test precision are evaluated.

The implementation solution of the present invention is as shown in FIG. 3*a*. The circuits 100*b*, 200*a* and the circuits 100*b*, 300*a* are used as control circuits for maintaining the bias voltage of the sensor. The circuits 100*b*, 210 and the circuits 100*b*, 310 are used as measurement circuits for detecting an sample to be tested. The measurement circuits and the control circuits are switched by means of the changeover switches 900*a* and 900*b*. The measurement circuits 100*b*, 210, 310 are used when the sensor is in operation and use an external power supply during operation; and the control circuits 100*b*, 200*a*, 300*a* are used when the sensor is in a standby state, so as to maintain the bias voltage of the sensor, and a button battery power supply is used. Power consumption of the circuits and conditions of test precision are evaluated.

In the implementation solution of the present invention, the measurement circuits use the external power supply when the sensor is in operation, so that the power consumption of the circuits in this state is not included in the calculation; however, switching between the standby state and the operation state is avoided in Comparison solution 1 and Comparison solution 2, so that a power supply of the sensor needs to be used all the time for consumption. The power consumption of batteries of the sensor is compared in this evaluation test.

In this evaluation test, the electrochemical sensor is a nitric oxide gas sensor with four-electrodes; the low-powerconsumption operational amplifiers U1, U2, U4 are MCP6041 from the Microchip Technology company, and low-noise operational amplifiers U3, U5 are ADA4622 from the Analog Devices company; and concentrations of nitric oxide in tested gas samples are 0 ppb and 35 ppb. R1 and R2 are 10 kΩ, R3, R5, R7 and R9 select 10-100Ω, R4, R6, R8 and R10 select 100-200 kΩ, C1 selects 0.1 uF, and C2, C3, C4 and C5 select 1-10 uF. The models of components on the circuits are specifically considered and selected according to actual measurement signal bandwidth requirements and noise levels.

Figure 4A:
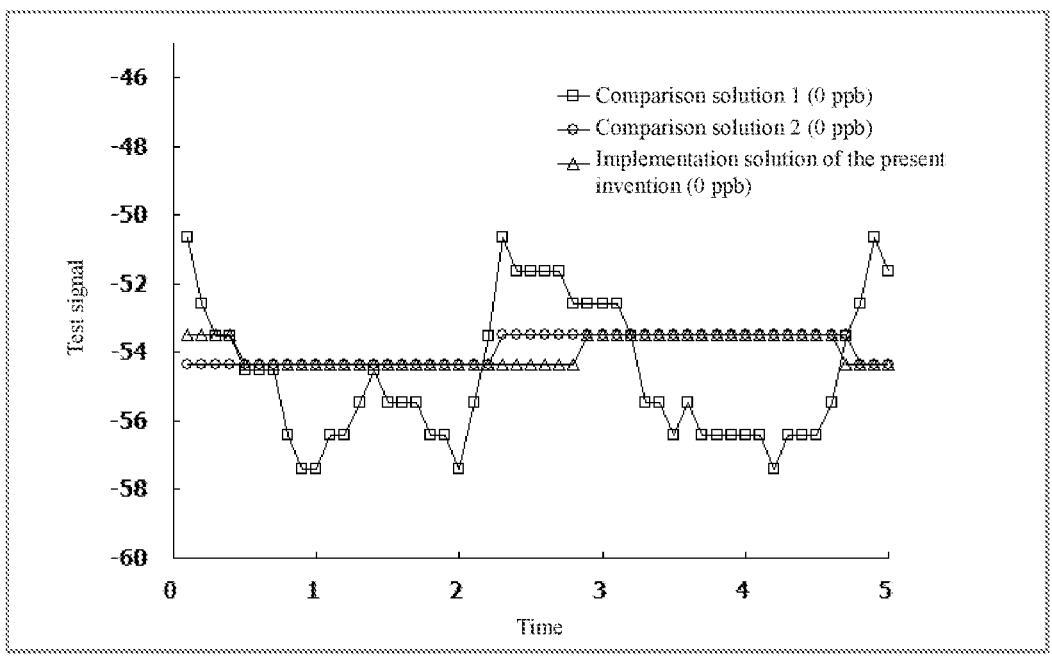
FIG. 4a: a measurement signal fluctuation comparison diagram in a stable period of comparison and evaluation, with a selected sample concentration being 0 ppb.
Figure 4B:
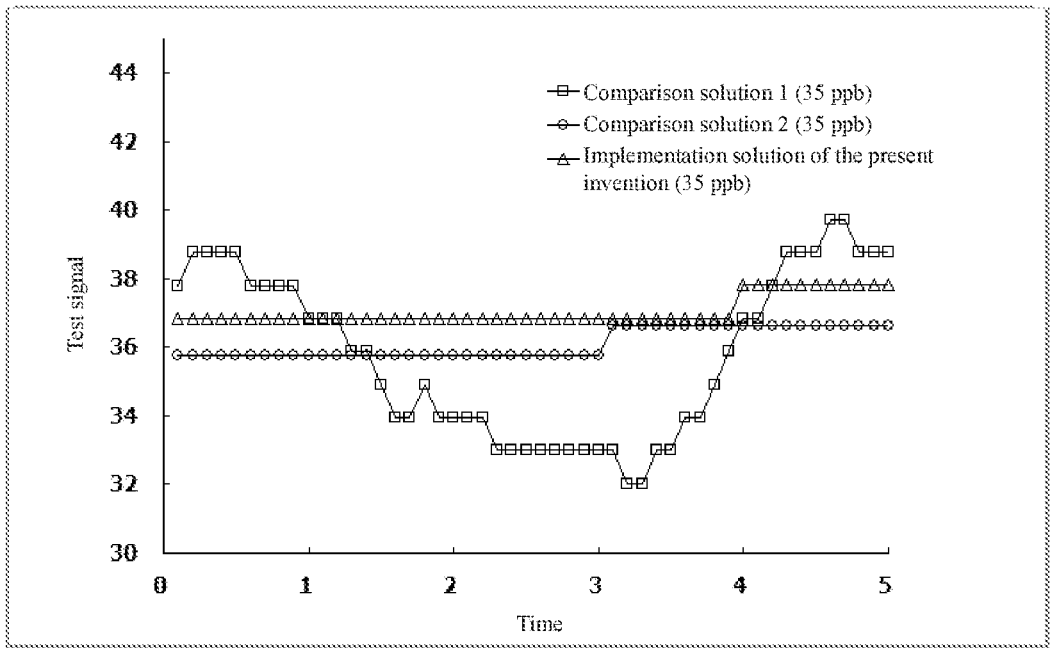
FIG. 4b: a measurement signal fluctuation comparison diagram in a stable period of comparison and evaluation, with a selected sample concentration being 35 ppb.

During test, after test signals are stabilized, the test signals are kept for 5 s, one signal is collected every 0.1 s, and the standard deviation of the signals is calculated. Comparison results are as shown in Table 1, and the comparisons of test signal fluctuations in stable periods of the various solutions are as shown in FIG. 4a and FIG. 4b.

TABLE 1

Results of Comparison and Evaluation

| Circuit solution | Power consumption of circuit | Standard deviation of signal 0 ppb | Standard deviation of signal 35 ppb |
|---|---|---|---|
| Comparison solution 1 | 2.7 uA (low power consumption) | 2.05 | 2.44 |
| Comparison solution 2 | 1201.5 uA (high power consumption) | 0.44 | 0.43 |
| Implementation solution of the present invention | 2.7 uA (low power consumption) | 0.44 | 0.42 |

The results show that, since the low-power-consumption operational amplifiers are used in Comparison solution 1, the measurement precision is significantly poor, and the measurement curve fluctuates significantly. Since the high-power-consumption operational amplifiers are used in Comparison solution 2, the power consumption is obviously increased. In the implementation solution of the present invention, the high-precision operational amplifiers are used in the measurement circuits, and low-precision and low-power-consumption operational amplifiers are used in the control circuits, so that the low power consumption is guaranteed, the precision of the measurement signals is also guaranteed, and the measurement curve is stable and free of significant fluctuations. The comparison and evaluation results fully illustrate the technical advantages of the solutions of the present invention.

Embodiment 5: Detection Equipment for Analyzing a Component in Expiratory Gas

Figure 8A:
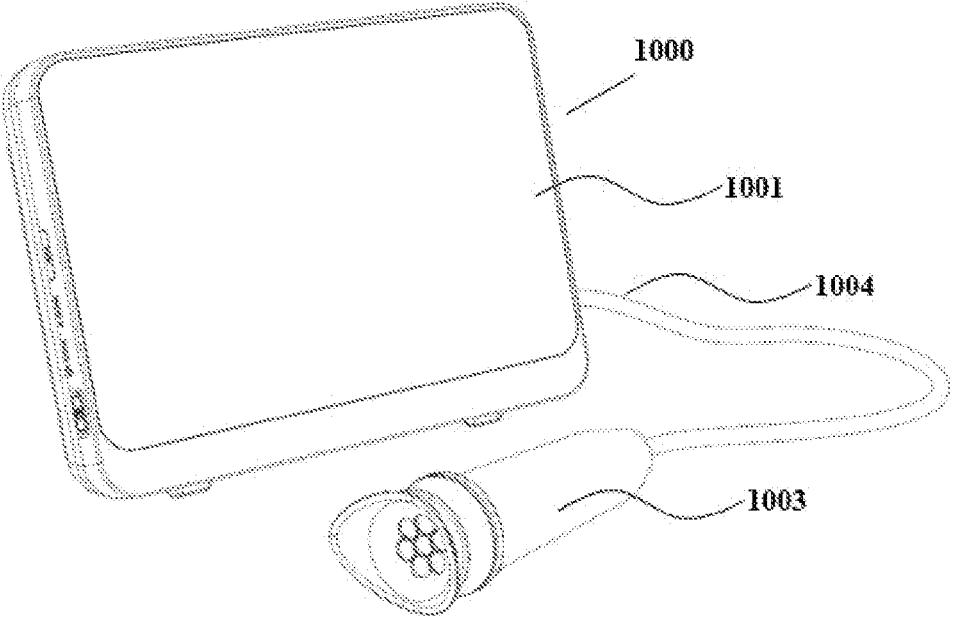
FIG. 8a: a front view of detection equipment for analyzing a component in expiratory gas.
Figure 8B:
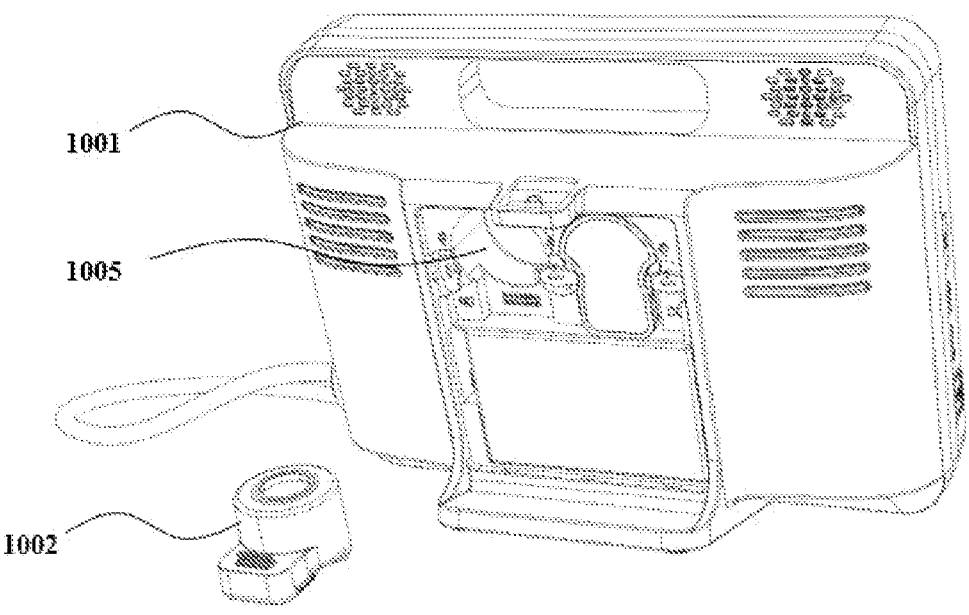
FIG. 8b: a rear view of the detection equipment for analyzing the component in the expiratory gas.

Detection equipment 1000 for analyzing a specific component in expiratory gas, as shown in FIG. 8a and FIG. 8b, can be used to detect components in expiratory gas, for example, nitric oxide, carbon monoxide, hydrogen, ammonia gas, hydrogen sulfide and oxygen. The detection equipment 1000 comprises a detection equipment host 1001, a specific component detector 1002 and a breathing handle 1003. According to gas collection and detection requirements, the detection equipment host 1001 can be internally configured with following components or some of the components: gas pipelines, gas flow control modules, gas sample temporary storage chambers, gas pumps, solenoid valves, three-way valves, gas humidity balance devices (such as Nafion tubes), specific gas component filtering tubes for zero-point tests, detection gas chambers of specific gas component detectors, temperature detection modules, humidity detection modules, atmospheric pressure detection modules, air flow pressure detection modules, gas flow detection modules, display screens, power modules, circuit hardware systems and software systems. The specific component detector 1002 comprises an electrochemical sensor for detecting a specific component, a circuit based on the technique of the present invention, a battery, a connecting plug-in component and a housing; and the specific component detector 1002 is mounted in a detector mounting recess 1005 in the detection equipment host 1001. The breathing handle 1003 is connected to a gas passage of the detection equipment host 1001 by means of a gas guiding tube 1004, and is used to collect a human expiratory gas sample. The breathing handle 1003 may be configured with a filtering box for filtering a specific gas component, which is used to enable a human body to inhale gas without the specific gas component firstly during detection, for example, when nitric oxide in the expiratory gas is detected, the filtering box of the breathing handle 1003 is provided with a potassium permanganate filtering material, and by means of the filtering box, during detection, the human body firstly inhales air with nitric oxide filtered out. According to the breathing handle 1003, through arrangement of an internal check valve, the gas can be inhaled from the air during inhalation, and the expiratory gas sample can be sent into the gas passage of the detection equipment host during expiration.

In this embodiment, detection of nitric oxide in the expiratory gas is used as an implementation example, wherein a nitric oxide detector 1002 is a four-electrode nitric oxide electrochemical sensor in Embodiment 3, a circuit adopts the technique of the present invention as shown in FIG. 3b, and a button battery CR2032 is included in the circuit for power supply. As a component, the nitric oxide detector 1002 may be stored and transported separately; and in the storage process at ordinary times, the nitric oxide detector applies a bias voltage to the electrochemical sensor by means of an internal button battery power supply and a low-power-consumption control circuit on the circuit, so as to ensure that the detector is in a stable state that the detector is "ready for work". According to measured data, when the detector of the present invention is stored separately, one button battery can ensure that the detector is in the stable state that the detector is "ready for work" for two years or longer, but products of the prior art in the current market can only guarantee three to six months. Therefore, the nitric oxide detector based on the technique of the present invention can guarantee the long-term effectiveness during separate storage or transportation before the detector is mounted on the detection equipment host, and can avoid the inconvenience caused by replacement of the battery due to exhausting of battery power and a relatively-long stabilization time caused by the replacement, so that the product is easier and more convenient to use.

Preferably, after the nitric oxide detector 1002 is mounted on the detection equipment host 1001, the detection equipment host 1001 can detect mounting of the detector, and a power supply of the detection equipment host is used for power supply, so that the power consumption of the button battery on the detector is further reduced.

Further, the detection equipment for nitric oxide in the expiratory gas in this embodiment and a standard nitric oxide gas are used for detection and analysis, two gas concentrations (24 ppb and 63 ppb) are tested, each concentration is repeatedly tested for three times, six values of a stable section of a reaction curve are taken in each test, one value is taken per second, the average value of the six values is taken as a result of each test, and results are shown in Table 2. As can be seen from Table 2, the six values detected by the nitric oxide detection equipment based on the technique of the present invention each time are stable and have small fluctuations, and the detection results of three times of repeated detection are high in repeatability.

TABLE 2

| Detection Results of Standard Nitric Oxide Gas | | | | | |
|---|---|---|---|---|---|
| | Concentration of standard nitric oxide gas | | | | |
| | 24 ppb | | | 63 ppb | | |
| Test result (ppb) | Test 1 | Test 2 | Test 3 | Test 1 | Test 2 | Test 3 |
| Test value 1 | 25.7 | 25.9 | 25.8 | 63.1 | 63.4 | 63.5 |
| Test value 2 | 25.8 | 25.9 | 25.9 | 63.2 | 63.4 | 63.5 |
| Test value 3 | 25.9 | 25.9 | 26.1 | 63.4 | 63.4 | 63.6 |
| Test value 4 | 25.8 | 26.0 | 26.0 | 63.6 | 63.3 | 63.8 |
| Test value 5 | 25.9 | 26.1 | 25.9 | 63.5 | 63.5 | 63.7 |
| Test value 6 | 25.8 | 26.1 | 26.0 | 63.3 | 63.3 | 63.5 |
| Average value in single test | 25.8 | 26.0 | 26.0 | 63.4 | 63.4 | 63.6 |
| Standard deviation in single test | 0.08 | 0.10 | 0.10 | 0.19 | 0.08 | 0.13 |
| Variable coefficient in single test | 0.3% | 0.4% | 0.4% | 0.3% | 0.1% | 0.2% |
| Average value of tests | | 25.9 | | | 63.4 | |
| Standard deviation of tests | | 0.09 | | | 0.14 | |
| Variable coefficient of tests | | 0.3% | | | 0.2% | |

Data of this embodiment indicates that, on the basis of the technique of the present invention, the long-term effectiveness of the detector during separate storage or transportation before the detector is mounted on the detection equipment host can be guaranteed, and the inconvenience caused by replacement of the battery due to exhausting of the battery power and the relatively-long stabilization time caused by the replacement can be avoided, and meanwhile, it is also ensured that the test values of each time of detection are stable and small in fluctuation, and the repeatability among the tests is high.

What is claimed is:

1. A method of regulating the power consumption rate of a main circuit associated with an electrochemical sensor, the main circuit comprising:

a control circuit configured and arranged to maintain a first bias voltage across the electrochemical sensor;

a measurement circuit configured and arranged to detect one or more signals from the electrochemical sensor during sample analysis;

an operational amplifier U2 disposed on the control circuit; and an operation amplifier U3 disposed on the measurement circuit wherein the control circuit is configured to operate at a first power consumption rate, the measurement circuit is configured to operate at a second power consumption rate, and the first power consumption rate is lower than the second power consumption rate, the method comprising:

maintaining the first bias voltage across the electrochemical sensor by operating the control circuit only when the electrochemical sensor is not in operation; and operating the measurement circuit only when the electrochemical sensor is in operation; thereby regulating the power consumption rate of the main circuit.

2. The method according to claim 1, wherein the electrochemical sensor comprises:

a working electrode and the operational amplifier U2 arranged on the control circuit is electrically connected to the working electrode, and the operational amplifier U3 arranged on the measurement circuit is electrically connected to the working electrode, wherein the operational amplifier U2 is configured to operate at a third power consumption rate and the operational amplifier U3 is configured to operate at a fourth power consumption, wherein the third power consumption rate is lower than the fourth power consumption rate, and the operational amplifier U3 is configured to produce noise at a first volume and the the the operational amplifier U2 is configured to produce noise at a second volume wherein the first volume is lower than the second volume; and a changeover switch disposed between the control circuit and the measurement circuit.

3. The method according to claim 2, wherein the operational amplifier U3 is configured to operate at a first precision and the operational amplifier U2 is configured to operate a second precision, wherein the first precision is higher than the first precision.

4. The method according to claim 2, wherein the operational amplifier U2 is configured to operate under a first working current below 10 uA.

5. The method according to claim 2, wherein the operational amplifier U3 is configured to produce a frequency noise under 1 microvolt peak-to-peak (uVpp) within 0.1 and 10 Hz.

6. The method according to claim 2, wherein the electrochemical sensor comprises:

a working electrode;

a counter electrode; and wherein the operational amplifier U2 comprises a first output and first non-inverting input end connected to the working electrode through the first inverted input end, the first output and the changeover switch; and the operational amplifier U3 comprises a second output end and second non-inverting input end connected to the working electrode through the second inverted input end, the second output end and the changeover switch; the method further comprising:

inputting a second bias voltage into the first non-inverting input end; and inputting a third bias voltage into the second non-inverting input end.

7. The method according to claim 6, wherein the electrochemical sensor further comprises a reference electrode; and the circuit further comprises an operation amplifier U1 comprising a third output end connected to the counter electrode and a third non-inverting input end connected to the reference electrode, the method further comprising inputting a reference voltage into the third non-inverting input end.

8. The method according to claim 6, wherein the electro-chemical sensor further comprises an auxiliary electrode, an operational amplifier U4 comprising a fourth output and a non-inverting input end connected to the auxiliary amplifier U4 and to the changeover switch and an operational ampli- fier U5 comprising a fifth output end and a fifth non-inverting end connected to the auxiliary electrode and to the changeover switch, wherein the method further comprises inputting a fourth bias voltage and a fifth bias voltage into the fourth non-inverting input end and the fifth non-inverting input end respectively.

9. The method according to claim 1, further comprising analyzing a specific component in an expiratory gas using the main circuit, wherein the specific component in the expiratory gas is selected from the group consisting of nitric oxide, carbon monoxide, hydrogen, ammonia gas, hydrogen sulfide, and oxygen.

10. The method according to claim 2, wherein the opera-tional amplifier U2 is configured to operate under a first working current below 1 uA.

11. The method according to claim 2, wherein the opera-tional amplifier U3 is configured to produce a frequency noise under 0.5 microvolts peak-to-peak (uVpp) within 0.1 and 10 Hz.

* * * * *